US007255718B1

(12) United States Patent
Akram et al.

(10) Patent No.: US 7,255,718 B1
(45) Date of Patent: Aug. 14, 2007

(54) PHOSPHATE-TYPE TENSIDES COMBINED WITH HAIR CONDITIONING AGENTS IN HAIR COLORING COMPOSITIONS

(75) Inventors: Mustafa Akram, Hamburg (DE); Wolfgang Wolff, Bargteheide (DE); Sandra Rohweder, Hamburg (DE)

(73) Assignee: Hans Schwarzkopf GmbH & Co. KG, Hamburg (DE)

( * ) Notice: Subject to any disclaimer, the term of this patent is extended or adjusted under 35 U.S.C. 154(b) by 0 days.

(21) Appl. No.: 09/937,912

(22) PCT Filed: Mar. 22, 2000

(86) PCT No.: PCT/EP00/02538

§ 371 (c)(1), (2), (4) Date: Jan. 24, 2002

(87) PCT Pub. No.: WO00/59457

PCT Pub. Date: Oct. 12, 2000

(30) Foreign Application Priority Data

Apr. 1, 1999 (DE) ................................ 199 14 927

(51) Int. Cl.
*A61K 7/13* (2006.01)
(52) U.S. Cl. .................. 8/405; 8/406; 8/407; 8/408; 8/410; 8/411; 8/415; 8/416; 8/421; 8/424; 8/437; 8/451; 8/466; 8/516; 8/540; 8/547; 8/548; 8/554; 8/581; 8/584; 8/606
(58) Field of Classification Search ............ 8/405, 8/406, 408, 410, 411, 415, 416, 421, 424, 8/437, 451, 466, 516, 540, 547, 548, 554, 8/581, 584, 606
See application file for complete search history.

(56) References Cited

U.S. PATENT DOCUMENTS

| 4,209,449 | A | * | 6/1980 | Mayhew et al. ............ 260/403 |
| 4,865,774 | A | | 9/1989 | Fabry et al. ................. 252/554 |
| 4,931,218 | A | | 6/1990 | Schenker et al. ............ 252/551 |
| 5,275,761 | A | | 1/1994 | Bergmann ................... 252/551 |
| 5,294,726 | A | | 3/1994 | Behler et al. ................. 554/98 |
| 5,358,667 | A | | 10/1994 | Bergmann ................... 252/547 |
| 5,456,863 | A | | 10/1995 | Bergmann ................... 252/547 |
| 5,494,489 | A | * | 2/1996 | Akram et al. ................. 8/408 |
| 5,534,267 | A | | 7/1996 | Neunhoeffer et al. ........ 424/701 |
| 5,580,357 | A | * | 12/1996 | Cotteret et al. ................. 8/408 |
| 5,843,193 | A | * | 12/1998 | Hawkins et al. ............... 8/408 |
| 5,938,792 | A | | 8/1999 | Lang et al. .................... 8/409 |
| 6,099,592 | A | | 8/2000 | Vidal et al. .................... 8/409 |

FOREIGN PATENT DOCUMENTS

| DE | 37 23 354 | 1/1989 |
| DE | 37 25 030 | 2/1989 |
| DE | 39 26 344 | 2/1991 |
| DE | 44 08 506 | 9/1995 |
| EP | 0 013 713 | 8/1980 |
| EP | 0 566 049 | 10/1993 |
| EP | 0 740 931 | 11/1996 |
| EP | 0 872 229 | 10/1998 |
| WO | WO92/18093 | 10/1992 |
| WO | WO94/08970 | 4/1994 |
| WO | WO97/14406 | 4/1997 |
| WO | WO98/56333 | 12/1998 |

OTHER PUBLICATIONS

The Science of Hair Care, Chapter 7, pp. 235-261, published as vol. 7 of Dermatology, Marcel Dekker Inc., NY/Basle (1986).
The Science of Hair Care, Chapter 8, pp. 263-286, published as vol. 7 of Dermatology, Marcel Dekker Inc., NY/Basle (1986).

* cited by examiner

*Primary Examiner*—Eisa Elhilo
(74) *Attorney, Agent, or Firm*—John S. Child, Jr.

(57) ABSTRACT

The present invention relates to a composition for coloring keratin fibers and a method of use thereof. The coloring composition contains at least one phosphate-based tenside of a particular formula, at least one conditioning component, and at least one dye and/or dye precursor.

15 Claims, No Drawings

PHOSPHATE-TYPE TENSIDES COMBINED WITH HAIR CONDITIONING AGENTS IN HAIR COLORING COMPOSITIONS

CROSS REFERENCE TO RELATED APPLICATIONS

This application is a national stage application under 35 U.S.C. § 371 of international application PCT/EP00/02538 filed on Mar. 22, 2000, the international application not being published in English. This application also claims priority under 35 U.S.C. § 119 to DE 199 14 927.5, filed on Apr. 1, 1999.

FIELD OF THE INVENTION

The present invention relates to a care active ingredient combination for the treatment of keratin fibers, in particular human hair, to hair coloring compositions which comprise this combination, and to the use of this active ingredient combination in hair coloring compositions.

BACKGROUND OF THE INVENTION

The cleansing and care of the hair is an important part of human bodycare. Both the cleansing of the hair using shampoos and also the decorative arrangement of the hairstyle, for example by coloring or permanent waving, are interventions which influence the natural structure and the properties of the hair.

Thus, for example, customary hair coloring compositions are formulated on the basis of oxidation dyes. Combinations of oxidation dyes and substantive dyes are frequently used to achieve specific shades. Colorants based on oxidation dyes lead to brilliant and permanent color shades. However, they require the use of strong oxidizing agents such as, for example, hydrogen peroxide solution. This can damage the hair to be colored. This damage must then be counteracted using suitable care products.

For this reason, it has been customary for some time to subject the hair to a special after-treatment. For this, the hair is treated with special active ingredients, for example quaternary ammonium salts or special polymers, usually in the form of a rinse. Depending on the formulation, this treatment improves combability, hold and fullness of the hair and reduces the proportion of split-ends.

Furthermore, "combination preparations" have recently been developed in order to reduce the time and effort of customary multistage procedures, in particular in the case of direct application by consumers.

As well as the customary components, for example for coloring the hair, these preparations additionally comprise active ingredients which were previously reserved for hair after-treatment agents. The consumer thus saves an application step; at the same time, the packaging cost is reduced since one product is used less.

The active ingredients which are available both for separate after-treatment agents and also for combination preparations can still not satisfy all of the wishes of the consumer.

There is therefore still a need for active ingredients and active ingredient combinations with good care properties and good biodegradability for which undesired accumulations on the hair are excluded.

Surprisingly, it has now been found that a combination of certain cationic tensides with further conditioning substances do not have the abovementioned disadvantages and at the same time improve the feel, wet combability and the shine of the treated hair.

DETAILED DESCRIPTION OF THE INVENTION

The invention thus firstly provides agents for the care treatment of keratin fibers, in particular human hair, which comprise at least one tenside of the formula (I)

and at least one conditioning component.

In the formula (I), y is an integer from 0 to 2, x is an integer from 1 to 3 with the proviso that the sum of x and y is 3.

In the tensides to be used according to the invention, M is additionally hydrogen, an equivalent of an alkali metal or alkaline earth metal cation, an ammonium cation or an alkyl radical having 1 to 4 carbon atoms, which is optionally substituted by one or more hydroxyl group(s). Particular preference is given to compounds in which M is a sodium cation.

Furthermore, B in the formula (I) of the tensides to be used according to the invention is an equivalent of a physiologically compatible anion. Examples of suitable anions are chloride, bromide, iodide, sulfate, perchlorate, tetrafluoroborate, tetraphenylborate and tetrachloridezincate. Preference is given to the chloride ion.

R in the tensides of the formula (I) according to the invention is a radical of the formula (II),

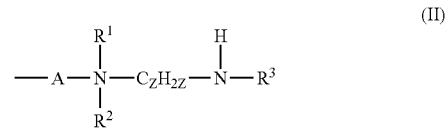

in which z is an integer from 1 to 4, in particular 3, and $R^1$ and $R^2$, independently of one another, are a $C_1$-$C_4$-alkyl radical, which is optionally substituted by one or more hydroxyl group(s) or an acyl group.

According to the invention, A is one of the units $-O-CH_2-CH_2-CH_2-$, $-O-CH_2-CH_2-$ or $-O-CH_2-CHOH-CH_2-$, the unit $-O-CH_2-CHOH-CH_2-$ being particularly preferred.

The radical $R^3$ is (a) a branched or unbranched, saturated $C_8$-$C_{18}$-acyl radical or (b) a branched or unbranched, mono- or polyunsaturated $C_8$-$C_{18}$-acyl radical.

Particularly preferred saturated radicals $R^3$ are the radicals of stearic acid, and the radicals of the mixture of the fatty acids which are obtained from coconut oil.

A particularly preferred unsaturated radical $R_3$ is the radical of linoleic acid. Surprisingly, it has been found that compounds of the formula (I) in which $R^3$ is the radical of linoleic acid are characterized by higher compatibility with the emulsifier system. This means that the substances can be incorporated more easily into the formulations. Furthermore, formulations containing compounds of the formula (I) in which $R^3$ is the radical of linoleic acid has a significantly higher care effect compared with compounds containing saturated fatty acid radicals.

Examples of the $C_1$-$C_4$-alkyl groups mentioned as substituents in the compounds according to the invention are the groups methyl, ethyl, propyl, isopropyl and butyl. Ethyl and methyl groups are preferred alkyl groups. Very particular preference is given to methyl groups.

Compounds of the formula (I) are already known. Thus, EP-A1-13 713 describes the surface-active properties of these compounds in general. In addition, the use of a compound of the formula (I) in hair coloring compositions is already known from DE-A1-44 08 506. However, these specifications give no indications of the synergistic increase in the care effect of the active ingredient combinations according to the invention.

Very particularly preferred compounds of the formula (I) are the substances known under the INCI names Linoleamidopropyl PG-Dimonium Chloride Phosphate, Cocamidopropyl PG-Dimonium Chloride Phosphate and Stearamidopropyl PG-Dimonium Chloride Phosphate. These are sold, for example, by Mona under the trade names Phospholipid EFA®, Phospholipid PTC® and Phospholipid SV®.

According to the invention, the compounds of the formula (I) are used in the claimed agents in amounts of from 0.1 to 5% by weight, in particular in amounts of from 0.2 to 2% by weight, in each case based on the total agent.

According to the invention, preferred conditioning active ingredients are the low molecular weight quaternary compounds. Particular preference is given to ammonium halides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride.

Very particularly preferred compounds are the halides of the cetyltrimethylammonium cation, in particular the bromide.

The preferred quaternary ammonium compounds also include the quaternary ester compounds, so-called "ester quats", such as the methylhydroxyalkyldialkoyloxyalkylammonium methosulfates sold under the trade name Stepantex®, and the product sold under the trade name Dehyquart®. Very particular preference is given to the mixture of fatty alcohols with methyltriethanolammonium methylsulfate dialkyl esters sold under the trade name Dehyquart® F75.

A further preferred group of quaternary ammonium compounds are the quaternized derivatives of imidazoline, such as, for example, the product sold under the trade name Rewoquat® W75 PG (INCI name: Quaternium-27).

As conditioning active ingredients, preference may also be given to cationic polymers. These are polymers which usually contain a quaternary nitrogen atom, for example in the form of an ammonium group.

Preferred cationic polymers are, for example,
quaternized cellulose derivatives, as are commercially available under the names Celquat® and Polymer JR®. The compounds Celquat® H 100, Celquat® L 200 and Polymer JR® 400 (INCI name: Polyquaternium-10) are preferred quaternized cellulose derivatives.
Polymeric dimethyldiallylammonium salts and copolymers thereof with esters and amides of acrylic acid and methacrylic acid, and the free acids. The products available commercially under the names Merquat® 100 (poly(dimethyldialylammonium chloride)), Merquat® 280 (dimethyldiallylammonium chloride-acrylic acid copolymer), Merquat® 550 (dimethyldiallylammonium chloride-acrylamide copolymer), and Merquat® Plus 3300 (dimethyldiallylammonium chloride-acrylamide-acrylic acid terpolymer) are examples of such cationic polymers.
Copolymers of vinylpyrrolidone with quaternized derivatives of dialkylaminoacrylate and -methacrylate, such as, for example, vinylpyrrolidone-dimethylaminomethacrylate copolymers quaternized with diethyl sulfate. Such compounds are available commercially under the names Gafquat® 734 and Gafquat® 755. A further example of such a copolymer of vinylpyrrolidone and methacrylamido-propyltrimethylammonium chloride sold under the trade name Gafquat® HS 100.
Vinylpyrrolidone-methoimidazolinium chloride copolymers, as supplied under the name Luviquat®.
Quaternized polyvinyl alcohol
Polyquaternium-37, as sold under the trade name Salcare® SC96, and the polymers known under the names
Polyquaternium 2,
Polyquaternium 17,
Polyquaternium 18 and
Polyquaternium 27, with quaternary nitrogen atoms in the polymer main chain.

Preference is given to cationic polymers from the first four groups mentioned, and, in particular, the polymers sold under the trade name Mirapol® A15 (INCI name: Polyquaternium-2) and Gafquat® 755N (INCI name: Polyquaternium-11). Polyquaternium-2, in combination with the tensides of the formula (I), is a very particularly preferred conditioning component.

Particularly in the case of the combination of the compounds of the formula (I) with cationic polymers as conditioning components, surprisingly strong synergistic effects of the component have been observed with regard to the overall care effect.

A further group of conditioning components are the protein derivatives. The protein derivatives can be based on animal or vegetable proteins. Suitable starting substances are, for example, keratin, collagen, elastin, wheat proteins, milk proteins, egg white proteins, silk proteins, almond proteins, soya proteins and proteins from animal hides.

Corresponding protein hydrolyzates are obtained in each case as a product mixture from the acidically, basically and/or enzymatically catalyzed degradation of these proteins. One example of a protein hydrolyzate preferred according to the invention is the collagen derivative sold under the trade name Crotein® C (INCI name: hydrolyzed collagen).

Cationic derivatives are obtained by subsequent reaction with compounds which usually carry quaternary ammonium groups or by reaction with corresponding amines and subsequent quaternization. A series of such quaternary protein hydrolyzates are commercial products available, for example, under the trade names Lamequat® L (cationic collagen hydrolyzate; INCI name: Lauryldimonium Hydroxypropylamino Hydrolyzed Animal Protein; Henkel), Croquat® WKP (animal keratin hydrolyzate; INCI name: Aqua, Cocodimonium Hydroxypropyl Hydrolyzed Keratin; Croda), Hydrotriticum® QL (cationic wheat protein hydrolyzate; INCI name: Lauryldimonium Hydroxypropyl Hydolyzed Wheat Protein; Croda) and Crotein® Q (cationic collagen hydrolyzate; INCI name: Hydroxypropyltrimonium Hydrolyzed Collagen; Croda).

In a first preferred embodiment, protein derivatives of an animal origin are preferred. Particular preference is given to the protein hydrolyzates of animal keratin. Since the composition with regard to the amino acid sequences present is very similar to that of human hair, a high affinity of such products to human hair results. Examples thereof are the products sold under the trade names Nutrilan® Keratin W and Promois® WK.

However, according to a further embodiment of the present invention, it may also be preferred to use protein derivatives of a vegetable origin. A preferred vegetable protein hydrolyzate is the quaternary wheat protein hydrolyzate sold under the trade name Gluadin® WQ.

In addition, quaternized galactomannan polysaccharides are preferred conditioning agents. Galactomannan polysaccharides preferred according to the invention are the quaternary guar gum derivatives, in particular quaternary hydroxy-$C_2$-$C_4$-alkyl guar gums, i.e. the quaternary propylene glycol ethers of guar gum, in particular the hydroxypropyl guar hydroxypropyltrimonium chloride. Some suitable derivatives are, for example, quaternary hydroxyethyl guar and quaternary hydroxybutyl guar. Suitable commercial products are, for example, sold under the trade names Jaguar® C-17 and Jaguar® C-162. A further group of suitable galactomannans are the quaternary polysaccharides obtained from the fruits of the carob tree.

In a further embodiment of the present compound, the conditioning components are chosen from the silicone oils. Silicone oils which may be used are, for example, the following compounds:

oligomeric polydimethylcyclosiloxanes (INCI name: Cyclomethicone), in particular the tetramer and pentamer compound, hexamethyldisiloxane, polyphenylmethylsiloxane (INCI name: Phenyl Trimethicone), dimethylsiloxane/dimethylpolysiloxanol mixtures (INCI name: Cyclomethicone (and) Dimethiconol), silicone-glycol copolymers (INCI name: Dimethicone Copolyol), aminofunctional polydimethylsiloxanes and hydroxylamino-modified silicones.

Such compounds are available commercially. Known commercial products are, for example, DC®344 Fluid, DC®345 Fluid, DC®200 Fluid, DC®556, DC®190, DC®193 SU and DC®Q2-1401 from Dow Corning, and the products Abil®K4, Abil®K520 and Abil®B8839 from Th. Goldschmidt AG.

Particular preference is given to the dimethylsiloxane/dimethylpolysiloxanol mixtures and the amino-group-containing silicone oils, such as, for example, the commercially available products Q2-7224 (manufacturer: Dow Corning; a stabilized trimethylsilylamodimethicone), Dow Corning 939 Emulsion (comprising a hydroxylamino-modified silicone which is also referred to as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethylsiloxanes, quaternium-80). As conditioning active ingredients, it is also possible to use paraffin oils, synthetically prepared oligomeric alkenes, and vegetable oils, such as jojoba oil, sunflower oil, orange oil, almond oil, wheatgerm oil and peach kernel oil.

The conditioning components are preferably present in the compositions according to the invention in amounts of from 0.05 to 5% by weight, in particular from 0.1 to 2% by weight, in each case based on the total composition. In the case of silicone oils, amounts of from 0.05 to 10% by weight, in particular from 0.2 to 5% by weight, very particularly amounts of from 0.5 to 2% by weight, in each case based on the total composition, in the compositions according to the invention may be preferred.

The nature of the hair-treatment composition used according to the invention is not subject to any limitations in principle. The compositions according to the invention can either remain on the hair, or be washed out again after a contact time of from a few seconds up to 45 minutes. Examples of compositions used according to the invention are shampoos, rinses, cures, conditioning agents, tinting agents, colorants, permanent waving compositions, neutralizing agents, hairsprays and blow waving compositions. The use of the active ingredient combinations according to the invention in rinse-off products may be a preferred embodiment.

The present invention further provides hair-treatment compositions which comprise the above-described active ingredient combination and at least one dye precursor and/or at least one dye. The colorations achieved with the compositions according to the invention are characterized by their improved fastness properties coupled with significantly improved care condition of the fibers.

In a first embodiment of this subject-matter of the present invention, the dye precursor may be an oxidation dye precursor of the developer type. It is also possible to use two or more developers together in the compositions according to the invention.

Developer substances are usually aromatic or heterocyclic ring systems which are characterized by two reactive groups, generally hydroxyl or amino groups, which are in the ortho or para position relative to one another. Such compounds are, for example, primary aromatic amines with a further free or substituted hydroxyl or amino group in the para or ortho position, and also diaminopyridine derivates, heterocyclic hydrazone derivatives or 4-aminopyrazolone derivatives.

Developer components preferred according to the invention are p-phenylenediamine, p-tolylenediamine, p-aminophenol, o-aminophenol, 1-(2'-hydroxyethyl)-2,5-diaminobenzene, N,N-bis(2-hydroxyethyl)-p-phenylenediamine, 2-(2,5-diaminophenoxy)ethanol, 1-phenyl-3-carboxyamido-4-amino-5-pyrazolone, 4-amino-3-methylphenol, 2,4,5,6-tetraminopyrimidine, 2-hydroxy-4,5,6-triaminopyrimidine, 4-hydroxy-2,5,6-triaminopyrimidine, 2,4-dihydroxy-5,6-diaminopyrimidine, 2-dimethylamino-4,5,6-triaminopyrimidine, 2-hydroxymethylamino-4-aminophenol, 4,4'-diaminodiphenylamine, 4-amino-3-fluorophenol, 2-aminomethyl-4-aminophenol, 2-hydroxymethyl-4-aminophenol, bis(2-hydroxy-5-aminophenyl)-methane, 1,4-bis(4-aminophenyl)diazacycloheptane, 1,3-bis(N(2-hydroxyethyl)-N-(4-aminophenylamino))-2-propanol, 4-amino-2-(2- hydroxyethoxy)phenol, and 4,5-diaminopyrazole derivatives according to EP 0 740 931 and WO 94/08970, such as, for example, 4,5-diamino-1-(2'-hydroxyethyl)pyrazole.

Particularly preferred developer components are p-phenylenediamine, p-tolylenediamine, p-aminophenol, 1-(2'-hydroxyethyl)-2,5-diaminobenzene, 4-amino-3-methylphenol, 2-aminomethyl-4-aminophenol, 2,4,5,6-tetraminopyrimidine, 2-hydroxy-4,5,6-triaminopyrimidine and 4-hydroxy-2,5,6-triaminopyrimidine.

Furthermore, to nuance the achievable color shades, the compositions according to the invention may also comprise one or more coupler components. Coupler substances are frequently aromatic or heterocyclic ring systems which have two reactive groups in the meta position. The coupler components usually used are m-phenylenediamine derivatives, naphthols, resorcinol and resorcinol derivatives, pyrazolones and m-aminophenol derivatives.

Coupler components preferred according to the invention are m-aminophenol and derivatives thereof, such as, for example, 5-amino-2-methylphenol, 5-(3-hydroxypropylamino)-2-methylphenol, 3-amino-2-chloro-6-methylphenol, 2-hydroxy-4-aminophenoxyethanol, 3-amino-6-methoxy-2-methylaminophenol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-(ethylamino)-4-methylphenol and 2,4-dichloro-3-aminophenol, o-aminophenol and derivatives thereof, m-diaminobenzene and derivatives thereof, such as, for example, 2,4-diaminophenoxyethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2-hydroxyethyl-amino)-1-methylbenzene and 1-amino-3-bis(2'-hydroxyethyl)aminobenzene, o-diaminobenzene and derivatives thereof, such as, for example, 3,4-diaminobenzoic acid and 2,3-diamino-1-methylbenzene, di- or trihydroxybenzene derivatives, such as, for example, resorcinol, resorcinol monomethyl ether, 2-methylresorcinol, 5-methylresorcinol, 2,5-di-methylresorcinol, 2-chlororesorcinol, 4-chlororesorcinol, pyrogallol and 1,2,4-trihydroxybenzene, pyridine derivatives, such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-3,4-diaminopyridine, 2,6-dihydroxy-4-methylpyridine, 2,6-diaminopyridine, 2,3-diamino-6-methyoxypyridine and 3,5-diamino-2,6-dimethyoxypyridine, naphthalene derivatives, such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene, morpholine derivatives such as, for example, 6-hydroxybenzomorpholine and 6-aminobenzomorpholine, quinoxaline derivatives, such as, for example, 6-methyl-1,2,3,4-tetrahydroquinoxaline, pyrazole derivatives, such as, for example, 1-phenyl-3-methylpyrazol-5-one, indole derivatives, such as, for example, 4-hydroxyindole, 6-hydroxyindole and 7-hydroxyindole, methylenedioxybenzene derivatives, such as, for example, 3,4-methylenedioxyphenol, 1-hydroxy-3,4-methylenedioxybenzene, 1-amino-3,4-methylenedioxybenzene and 1-(2'-hydroxyethyl)amino-3,4-methylenedioxybenzene.

Particularly preferred coupler components are 1-naphthol, 1,5-, 2,7- and 1,7-dihydroxynaphthalene, 5-amino-2-methylphenol, resorcinol, 3-aminophenol, 4-chlororesorcinol, 2-chloro-6-methyl-3-aminophenol, 2-methylresorcinol, 5-methylresorcinol, 2,5-dimethylresorcinol, 2-amino-3-hydroxypyridine, and 2,6-dihydroxy-3,4-diaminopyridine.

The developer and coupler components are usually used in free form. In the case of substances with amino groups, it may, however, be preferred to use them in salt form, in particular in the form of hydrochlorides and sulfates.

The hair coloring compositions according to the invention comprise the developer components and also the coupler components preferably in amount of from 0.005 to 20% by weight, preferably 0.1 to 5% by weight, in each case based on the overall oxidation colorant. Developer components and coupler components are usually used in approximately equal molar amounts relative to one another. Although the equimolar feed has proven advantageous, a certain excess of individual oxidation dye precursors is not disadvantageous, meaning that developer components and coupler components may preferably be present in a molar ratio of from 1:0.5 to 1:2 in the colorant. The total amount of oxidation dye precursors is usually at most 20% by weight, based on the total composition.

According to a second preferred embodiment of the subject-matter of the present invention, the dye precursor may be a derivative of indoline of the formula (IIIa),

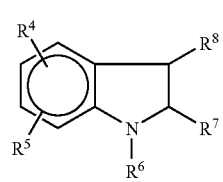

(IIIa)

in which, independently of one another, $R^6$ is hydrogen, a $C_1$-$C_4$-alkyl group or a $C_1$-$C_4$-hydroxyalkyl group, $R^7$ is hydrogen or a —COOH group, where the —COOH group may also be in salt form with a physiologically compatible cation, $R_8$ is hydrogen or a $C_1$-$C_4$-alkyl group, $R^4$ is hydrogen, a hydroxyl group, an amino group, a $C_1$-$C_4$-alkoxy group or a group —OCO—$R^9$, in which $R^9$ is a $C_1$-$C_4$-alkyl group, and $R^5$ is one of the groups mentioned under $R^4$, or a physiologically compatible salt of these compounds with an organic or inorganic acid, with the proviso that $R^4$ and $R^5$ are not hydrogen at the same time.

In a third preferred embodiment of the subject-matter of the present invention, the dye precursor may be a derivative of indole of the formula (IIIb),

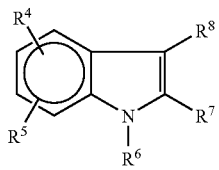

in which, independently of one another, $R^6$ is hydrogen, a $C_1$-$C_4$-alkyl group or a $C_1$-$C_4$-hydroxyalkyl group, $R^7$ is hydrogen or a —COOH group, where the —COOH group may also be in salt form with a physiologically compatible cation, $R^8$ is hydrogen or a $C_1$-$C_4$-alkyl group, $R^4$ is hydrogen, a hydroxyl group, an amino group, a $C_1$-$C_4$-alkoxy group or a group —OCO—$R^9$, in which $R^9$ is a $C_1$-$C_4$-alkyl group, and $R^5$ is one of the groups given under $R^4$, or a physiologically compatible salt of these compounds with an organic or inorganic acid, with the proviso that $R^4$ and $R^5$ are not hydrogen at the same time.

Preferred substances of the formula (IIIa) are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, 6-hydroxyindoline, 6-aminoindoline and 4-aminoindoline. Preferred substances of the formula (IIIb) are 5,6-dihydroxyindole, N-methyl-5,6-dihyroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-aminoindole and 4-aminoindole.

Very particular preference is given to 5,6-dihydroxyindole and 5,6-dihydroxyindoline.

In a first preferred variant of the embodiments described above, the compositions are formulated such that they comprise only indole derivatives and/or indoline derivatives of the formulae (IIIa) and (IIIb) as dye precursors and are free from customary oxidation dye precursors of the developer and/or coupler type.

In a second preferred variant of the embodiments described above, the compositions according to the invention may, in addition to the indole derivatives and/or indoline derivatives of the formulae (IIIa) and (IIIb), also comprise customary oxidation dye precursors of the developer and/or coupler type.

According to the invention, it may be particularly preferred to use the indole derivatives and/or the indoline derivatives of the formulae (IIIa) and (IIIb) in combination with one or more coupler components in hair coloring compositions. By way of example, express reference may be made at this point to the coupler components given above.

Furthermore, it may be preferred according to the invention to use the indole derivatives and/or indoline derivatives of the formulae (IIIa) and (IIIb) in combination with at least one amino acid or an oligo peptide in hair coloring compositions. According to the invention, it may also be preferred if the amino acid is an α-amino acid. Very particularly preferred α-amino acids are arginine, ornithine, lysine and histidine.

In a further preferred embodiment, the hair-treatment compositions according to the invention comprise substantive dyes. Substantive dyes are usually nitrophenylenediamines, nitroaminophenols, azo dyes, anthraquinones or indophenols. Preferred substantive dyes are the compounds known under the international names or trade names HC Yellow 2, HC Yellow 4, HC Yellow 5, HC Yellow 6, Basic Yellow 57, Disperse Orange 3, HC Red 3, HC Red BN, Basic Red 76, HC Blue 2, HC Blue 12, Disperse Blue 3, Basic Blue 99, HC Violet 1, Disperse Violet 1, Disperse Violet 4, Disperse Black 9, Basic Brown 16 and Basic Brown 17, and 4-amino-2-nitrodiphenylamine-2'-carboxylic acid, 6-nitro-1,2,3,4-tetrahydroquinoxaline, hydroxyethyl-2-nitrotoluidine, picramic acid, 2-amino-6-chloro-4-nitrophenol 4-ethylamino-3-nitrobenzoic acid and 2-chloro-6-ethylamino-1-hydroxy-4-nitrobenzene.

The compositions of the invention according to this embodiment comprise the substantive dyes preferably in an amount of from 0.01 to 20% by weight, based on the total colorant.

Furthermore, the preparations according to the invention may also comprise naturally occurring dyes, such as, for example, henna red, henna neutral, henna black, chamomile blossom, sandalwood, black tea, buckthorn bark, sage, logwood, madder root, catechu, indigo, sedre and alkanna root.

It is not necessary that the oxidation dye precursors or the substantive dyes are each uniform compounds. Rather, as a consequence of the preparation processes for the individual dyes, the hair coloring compositions according to the invention may also comprise further components in lesser amounts, provided these do not adversely affect the coloring result or do not have to be excluded for other reasons, e.g. toxicological reasons.

With regard to the dyes which can be used in the hair coloring compositions according to the invention, express reference is also made to the monograph Ch. Zviak, The Science of Hair Care, Chapter 7 (pages 248-250; substantive dyes), and chapter 8, pages 264-267; oxidation dye precursors), published as volume 7 of the series "Dermatology" (Ed.: Ch. Culnan and H. Maibach), Verlag Marcel Dekker Inc., New York, Basle, 1986, and the "European Inventory of Cosmetic Raw Materials", published by the European Community, available in floppy disk form from the Bundesverband Deutscher Industrie- und Handelsunternehmen für Arzneimittel, Reformwaren und Körperpflegemittel [Federal Association of German Industrial and Commercial Enterprises for Medicaments, Health Goods and Bodycare Products], Mannheim.

Colorations of particular color depth can be achieved if, in addition to the dyes and/or dye precursors, the compositions additionally comprise Meadowfoam Seed Oil (INCI name).

In a very particularly preferred embodiment of the present invention, the compositions comprise at least one dye and/or a dye precursor, polyquaternium-2 and the compound of the formula (I) known under the INCI name Linoleamidopropyl PG-Dimonium Chloride Phosphate.

For the preparation of the colorants according to the invention, the dye precursors are incorporated into a suitable aqueous, alcoholic or aqueous-alcoholic carrier. For the purposes of hair coloring, such carriers are, for example, creams, emulsions, liquids, gels or else tenside-containing foaming solutions, e.g. shampoos, foam aerosols or other preparations which are suitable for application to the hair.

For the purposes of the present invention, aqueous-alcoholic solutions are to be understood as meaning aqueous solutions comprising 3 to 70% by weight of a $C_1$-$C_4$-alcohol, in particular ethanol or isopropanol. The compositions according to the invention can additionally comprise further organic solvents, such as, for example, methoxybutanol, benzyl alcohol, ethyl diglycol or 1,2-propylene glycol. Preference is given here to water-soluble organic solvents.

The oxidative development of the coloration can in principle take place using atmospheric oxygen. However, preference is given to using a chemical oxidizing agent, particularly when a lightening effect on human hair is desired in addition to the coloration. Suitable oxidizing agents are persulfates, chlorites and, in particular, hydrogen peroxide or addition products thereof with urea, melamine, and also sodium borate. It is also possible to carry out the oxidation using enzymes. In this connection, the enzymes may serve to transfer atmospheric oxygen to the developer component or to intensify the effect of small amounts of oxidizing agent present. An example of an enzymatic process is the procedure to intensify the effect of small amounts (e.g. 1% and less, based on the overall composition) of hydrogen peroxide by peroxidases.

The preparation of the oxidizing agent is expediently mixed with the preparation from the oxidation dye precursors directly prior to hair coloring. The resulting ready-to-use hair coloring preparation should preferably have a pH in the range from 6 to 12. Particular preference is given to the use of the hair coloring composition in a weakly alkaline medium. The application temperatures may be in a range between 15 and 40° C. After a contact time of from 5 to 45 minutes, the hair coloring composition is removed from the hair to be colored by rinsing. Subsequent washing with a shampoo is dispensed with if a carrier with a high content of tenside, e.g. a color shampoo, has been used.

The hair-treatment compositions according to the invention may also comprise all active ingredients, additives and auxiliaries known for such preparations. In many cases, the compositions comprise at least one tenside, anionic and also zwitterionic, ampholytic, nonionic and cationic tensides being suitable in principle. In many cases, it has, however, proven advantageous to choose the tensides from anionic, zwitterionic or nonionic tensides.

Surprisingly, it has been found that anionic tensides can be incorporated into the compositions according to the invention without the formation of noteworthy precipitates with the cationic components.

Suitable anionic tensides in preparations according to the invention are all anionic surface-active substances suitable for use on the human body. These are characterized by a solubilizing, anionic group, such as, for example, a carboxylate, sulfate, sulfonate or phosphate group, and a lipophilic alkyl group having about 10 to 22 carbon atoms. Additionally, glycol or polyglycol ether groups, ester groups, ether groups and amide groups, and hydroxyl groups may be present in the molecule. Examples of suitable anionic surfactants are, in each case in the form of the sodium, potassium and ammonium and also the mono- di- and trialkanolammonium salts having 2 to 3 carbon atoms in the alkanol group, linear fatty acids having 10 to 22 carbon atoms (soaps)

ether carboxylic acids of the formula R—O—(CH$_2$—CH$_2$O)$_x$—CH$_2$—COOH, in which R is a linear alkyl group having 10 to 22 carbon atoms and x=0 or 1 to 16, acyl sarcosides having 10 to 18 carbon atoms in the acyl group, acyl taurides having 10 to 18 carbon atoms in the acyl group, acyl isethionates having 10 to 18 carbon atoms in the acyl group, sulfosuccinic mono- and dialkyl esters having 8 to 18 carbon atoms in the alkyl group and sulfosuccinic monoalkyl polyoxyethyl esters having 8 to 18 carbon atoms in the alkyl group and 1 to 6 oxyethyl groups, linear alkanesulfonates having 12 to 18 carbon atoms, linear alpha-olefinsulfonates having 12 to 18 carbon atoms, alpha-sulfo fatty acid methyl esters of fatty acids having 12 to 18 carbon atoms, alkyl sulfates and alkyl polyglycol ether sulfates of the formula R—O(CH$_2$—CH$_2$O)$_x$—SO$_3$H, in which R is a preferably linear alkyl group having 10 to 18 carbon atoms and x=0 or 1 to 12, mixtures of surface-active hydroxysulfonates according to DE-A-37 25 030, sulfated hyroxyalkylpolyethylene and/or hydroxyalkylene propylene glycol ethers according to DE-A-37 23 354, sulfonates of unsaturated fatty acids having 12 to 24 carbon atoms and 1 to 6 double bonds according to DE-A-39 26 344, esters of tartaric acid and citric acid with alcohols, which represent addition products of approximately 2-15 molecules of ethylene oxide and/or propylene oxide with fatty alcohols having 8 to 22 carbon atoms.

Preferred anionic tensides are alkyl sulfates, alkylpolyglycol ether sulfates and ether carboxylic acids having 10 to 18 carbon atoms in the alkyl group and up to 12 glycol ether groups in the molecule and, in particular, salts of saturated and, in particular, unsaturated $C_8$-$C_{22}$-carboxylic acids, such as oleic acid, stearic acid, isostearic acid and palmitic acid.

Zwitterionic tensides is the term used for those surface-active compounds which carry at least one quaternary ammonium group and at least one —COO$^{(-)}$ or —SO$_3^{(-)}$ group in the molecule. Particular suitable zwitterionic tensides are the betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and also cocoacylaminoethyl hydroxyethyl-carboxymethylglycinate. A preferred zwitterionic tenside is the fatty acid amide derivative known under the INCI name Cocamidopropyl Betaine.

Ampholytic tensides are to be understood as meaning those surface-active compounds which, apart from a $C_8$-$C_{18}$-alkyl or -acyl group in the molecule, contain at least one free amino group and at least one —COOH or —SO$_3$H group and are capable of forming internal salts. Examples of suitable ampholytic tensides are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic tensides are N-cocoalkylaminopropionate, cocoacylaminoethylamino-propionate and $C_{12-18}$-acylsarcosine.

Nonionic tensides contain, as hydrophilic group, e.g. a polyol group, a polyalkylene glycol ether group or a combination of polyol and polyglycol ether groups. Such compounds are, for example, addition products of from 2 to 30 mol of ethylene oxide and/or 0 to 5 mol of propylene oxide with linear fatty alcohols having 8 to 22 carbon atoms, with fatty acids having 12 to 22 carbon atoms and with alcohol phenols having 8 to 15 carbon atoms in the alkyl group, $C_{12-22}$-fatty acid mono- and diesters of addition products of from 1 to 30 mol of ethylene oxide with glycerol, $C_{8-22}$-alkyl mono- and -oligoglycosides and ethoxylated analogs thereof, addition products of from 5 to 60 mol of ethylene oxide with castor oil and hydrogenated castor oil, addition products of ethylene oxide with sorbitan fatty acid esters addition products of ethylene oxide with fatty acid alkanolamide.

Alkylamidoamines, in particular fatty acid amido amines, such as the stearylamidopropyldimethylamine available under the name Tego Amid®S 18, are characterized, as well as by a good conditioning action, in particular by their good biodegradability.

One example of a quaternary sugar derivative which can be used as cationic tenside is the commercial product Glucquat®100, according to INCI nomenclature a "Lauryl Methyl Gluceth-10 Hydroxypropyl Dimonium Chloride".

The compounds containing alcohol groups used as tensides may each be uniform substances. However, it is generally preferred to prepare the substances starting from native vegetable or animal raw materials, thus giving mixtures of substances having varying alkyl chain lengths depending on the raw material in question.

In the case of the tensides which represent addition products of ethylene and/or propylene oxide with fatty alcohols or derivatives of these addition products, it is possible to use either products with a "normal" homologue distribution and also those with a narrowed homologue distribution. Here, "normal" homologue distribution is to be understood as meaning mixtures of homologues obtained during the reaction of fatty alcohol and alkylene oxide using alkali metals, alkali metal hydroxides or alkali metal alkoxides as catalysts. Narrowed homologue distributions are, by contrast, obtained if, for example, hydrotalcites, alkaline earth metal salts of ether carboxylic acids, alkaline earth metal oxides, hydroxides or alkoxides are used as catalysts. The use of products with narrowed homologue distribution may be preferred.

Finally, the compositions according to the invention preferably also comprise a fatty substance.

Preferred fatty substances are linear and branched, saturated and unsaturated fatty alcohols or natural fatty alcohol mixtures having 8 to 22 carbon atoms in the alkyl chain, such as, for example, decanol, octanol, octenol, dodecenol, decenol, octadienol, dodecadienol, decadienol, oleyl alcohol, eruca alcohol, ricinoleic alcohol, stearyl alcohol, isostearyl alcohol, cetyl alcohol, lauryl alcohol, myristyl alcohol, arachidyl alcohol, caprylic alcohol, capric alcohol, linoleyl alcohol, linolenyl alcohol and behenyl alcohol, and Guerbet alcohols thereof, and also fatty alcohol sections which are produced by reducing naturally occurring triglycerides, such as beef tallow, palm oil, peanut oil, rapeseed oil, cottonseed oil, soyabean oil, sunflower oil and linseed oil, or fatty acid esters arising from their transesterification products with corresponding alcohols, and thus represent a mixture of different fatty alcohols. The fatty alcohols are usually used in amounts of from 0.01 to 15% by weight, preferably from 0.1 to 10% by weight and particularly preferably from 0.3 to 6% by weight, based on the total preparation.

As fatty substances, it is also possible to use monoesters of the fatty acids with alcohols having 6 to 24 carbon atoms, and triglycerides of natural origin.

Further active ingredients, auxiliaries and additives are, for example, nonionic polymers, such as, for example, vinylpyrrolidine/vinyl acrylate copolymers, polyvinylpyrrolidone and vinylpyrrolidone/vinyl acetate copolymers and polysiloxanes, zwitterionic and amphoteric polymers, such as, for example, acrylamidopropyltrimethylammonium chloride/acrylate copolymers and octylacrylamide/methyl methacrylate/tert-butylaminoethyl methacrylate/2-hydroxypropyl methacrylate copolymers, anionic polymers, such as, for example, polyacrylic acids, crosslinked polyacrylic acids, vinyl acetate/crotonic acid copolymers, vinyl-pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers, thickeners, such as agar-agar, guar gum, alginate, xanthan gum, gum arabic, karaya gum, carob seed grain, linseed gums, dextrans, cellulose derivatives, e.g. methylcellulose, hydroxyalkylcellulose and carboxymethylcellulose, starch fractions and derivatives, such as amylose, amylopektin and dextrins, clays, such as, for example, bentonite or completely synthetic hydrocolloids, such as, for example, polyvinyl alcohol, structurants, such as glucose and maleic acid, hair-conditioning compounds, such as phospholipids, for example soya lecithin, egg lecithin and cephalins, perfume oils, dimethyl isosorbide and cyclodextrins, solubility promoters, such as ethanol, isopropanol, ethylene glycol, propylene glycol, glycerol and diethylene glycol, antidandruff active ingredients, such as piroctone olamine and zinc omadine, further substances for setting the pH, active ingredients, such as panthenol, pantothenic acid, allantoin, pyrrolidonecarboxylic acids and salts thereof, plant extracts and vitamins, cholesterol, light protection agents, bodying agents, such as sugar esters, polyol esters or polyol alcohol ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration substances, such as glycerol, propylene glycol monoethyl ether, carbonates, hydrogencarbonates, guanidines, ureas and primary, secondary and tertiary phosphates, opacifiers, such as latex, pearlizing agents, such as ethylene glycol mono- and distearate, propellants, such as propane-butane mixtures, $N_2O$, diemthyl ether, $CO_2$ and air, and antioxidants.

The constituents of the water-containing carrier are used for the preparation of the hair-treatment compositions according to the invention in amounts customary for this purpose; e.g. emulsifiers are used in concentrations of from 0.5 to 30% by weight and thickeners are used in concentrations of from 0.1 to 25% by weight of the overall composition.

The present invention further provides for the use of the compositions of the present invention for coloring keratin fibers.

The examples below serve to illustrate the subject-matter of the present invention in more detail.

All amounts given in the examples are parts by weight.

EXAMPLE 1

| | |
|---|---:|
| Ammonium carbopol solution, 1% strength in water[1] | 17.25 |
| Ammonium rohagit solution, 6% strength in water[2] | 5.25 |
| Oleth-7[3] | 5.70 |
| Potassium olein soap, 12.5% strength in water | 12.75 |
| Potassium castor oil soap, 12.5% strength in water | 3.45 |
| Plantaren ® 2000[4] | 0.53 |
| Titanium dioxide anatase, type AS 05 | 0.48 |
| Cetiol ® V[5] | 3.45 |
| Cetyl alcohol | 16.80 |
| Glycerol monostearate NSE[6] | 2.85 |
| Phospholipid EFA[7] | 0.85 |
| Tetrasodium EDTA | 0.46 |
| Silica, highly dispersed, pyrogenic | 0.11 |
| p-Tolylenediamine | 2.41 |
| Resorcinol | 0.86 |
| 3-Aminophenol | 0.26 |
| 1-Methoxy-2-amino-4-(2-hydroxyethylamino)benzene | 0.11 |
| 1,2-Propylene glycol USP | 1.05 |
| Methoxybutanol | 1.43 |
| Ammonia, 25% strength in water | ad pH 9.0 |
| Ascorbic acid | 0.06 |
| Mirapol ® A15[8] | 0.19 |
| Perfume | 0.43 |
| Water | ad 100.00 |

[1] Solution of an ammonium salt of a methacrylic acid-methyl acrylate copolymer (INCI name: Ammonium Polyacrylate) (Röhm GmbH)
[2] Solution of an ammonium salt of an acrylic acid polymer (INCI name: Ammonium Acrylate Copolymer) (Goodrich)
[3] Oleyl alcohol with 7 EO units (Henkel)
[4] $C_{8-16}$-alkyl 1,4-polyglucoside (about 51% active substance; INCI name: Decyl Glucoside) (Henkel)
[5] Oleic acid decyl ester (INCI name: Decyl Oleate) (Henkel)
[6] (INCI name: Glyceryl Stearate) (Oleofina)
[7] Compound of the formula (I) (about 30% active substance; INCI name: Linoleamidopropyl PG-Dimonium Chloride Phosphate) (Mona)
[8] About 64% active substance; INCI name: Polyquaternium-2 (Rhodia)

This composition was mixed with an aqueous, 6% strength hydrogen peroxide solution in the ratio 1:1 and applied to a light brown, 80% gray normal hair tress. After a contact time of 30 min at 25° C., the tress was rinsed with water, subsequently shampooed and dried with a hairdryer.

The resulting tress had been colored dark brown and had very good gray coverage.

EXAMPLE 2

| | |
|---|---:|
| Ammonium carbopol solution, 1% strength in water | 17.25 |
| Ammonium rohagit solution, 6% strength in water | 5.25 |
| Oleth-7 | 5.70 |
| Potassium olein soap, 12.5% strength in water | 12.75 |
| Potassium castor oil soap, 12.5% strength in water | 3.45 |
| Plantaren ® 2000 | 0.53 |
| Titanium dioxide anatase, type AS 05 | 0.48 |
| Cetiol ® V | 3.45 |
| Cetyl alcohol | 16.80 |
| Glycerol monostearate NSE | 2.85 |
| Phospholipid EFA | 0.85 |
| Tetrasodium EDTA | 0.46 |
| Silica, highly dispersed, pyrogenic | 0.11 |
| p-Tolylenediamine | 2.12 |
| Resorcinol | 0.63 |
| 3-Aminophenol | 0.20 |
| 1-Methoxy-2-amino-4-(2-hydroxyethylamino)benzene | 0.05 |
| 1,2-Propylene glycol USP | 1.05 |
| Methoxybutanol | 1.43 |
| Ammonia, 25% strength in water | ad pH 10.0 |
| Ascorbic acid | 0.06 |
| Cetyltrimethylammonium bromide | 0.50 |
| Perfume | 0.43 |
| Water | ad 100.00 |

This composition was mixed with an aqueous, 6% strength hydrogen peroxide solution in the ratio 1:1 and applied to a dark blond, 50% gray normal hair tress. After a contact time of 30 min at 25° C., the tress was rinsed with water, subsequently shampooed and dried with a hairdryer.

The resulting tress had been colored light brown and had very good gray coverage.

EXAMPLE 3

| | |
|---|---:|
| Ammonium carbopol solution, 1% strength in water | 17.25 |
| Ammonium rohagit solution, 6% strength in water | 5.25 |
| Oleth-7 | 5.70 |
| Potassium olein soap, 12.5% strength in water | 12.75 |
| Potassium castor oil soap, 12.5% strength in water | 3.45 |
| Plantaren ® 2000 | 0.53 |
| Titanium dioxide anatase, type AS 05 | 0.48 |
| Cetiol ® V | 3.45 |
| Cetyl alcohol | 16.80 |
| Glycerol monostearate NSE | 2.85 |
| Phospholipid EFA | 0.85 |
| Tetrasodium EDTA | 0.46 |
| Silica, highly dispersed, pyrogenic | 0.11 |
| p-Tolylenediamine | 0.84 |
| Resorcinol | 0.21 |
| 3-Aminophenol | 0.05 |
| 4-Chlororesorcinol | 0.15 |
| 1,2-Propylene glycol USP | 1.05 |
| Methoxybutanol | 1.43 |
| Ammonia, 25% strength in water | ad pH 10.5 |
| Ascorbic acid | 0.06 |
| Rewoquat ® W 75 PG[9] | 0.30 |
| Perfume | 0.43 |
| Water | ad 100.00 |

[9] 1-Methyl-2-nortallow-alkyl-3-tallow fatty acid amidoethylimidazolinium methosulfate (about 75% active substance in propylene glycol; INCI name: Quaternium 27) (Witco Surfactants GmbH)

This composition was mixed with an aqueous, 6% strength hydrogen peroxide solution in the ratio 1:1 and applied to a medium blond, 50% gray normal hair tress. After a contact time of 30 min at 25° C., the tress was rinsed with water, subsequently shampooed and dried with a hairdryer.

The resulting tress had been colored dark blond and had very good gray coverage.

EXAMPLE 4

| | |
|---|---:|
| Ammonium carbopol solution, 1% strength in water | 17.25 |
| Ammonium rohagit solution, 6% strength in water | 5.25 |
| Oleth-7 | 5.70 |

| -continued | |
|---|---|
| Potassium olein soap, 12.5% strength in water | 12.75 |
| Potassium castor oil soap, 12.5% strength in water | 3.45 |
| Plantaren ® 2000 | 0.53 |
| Titanium dioxide anatase, type AS 05 | 0.48 |
| Cetiol ® V | 3.45 |
| Cetyl alcohol | 16.80 |
| Glycerol monostearate NSE | 2.85 |
| Phospholipid EFA | 0.85 |
| Tetrasodium EDTA | 0.46 |
| Silica, highly dispersed, pyrogenic | 0.22 |
| p-Tolylenediamine | 1.33 |
| Resorcinol | 0.48 |
| 3-Aminophenol | 0.10 |
| 1-Methoxy-2-amino-4-(2-hydroxyethylamino)benzene | 0.02 |
| 1,2-Propylene glycol USP | 1.05 |
| Methoxybutanol | 1.43 |
| Ammonia, 25% strength in water | ad pH 9.5 |
| Ascorbic acid | 0.06 |
| Polymer JR ® 400[10] | 1.00 |
| Perfume | 0.43 |
| Water | ad 100.00 |

[10]Quaternized hydroxyethylcellulose (INCI name: Polyquaternium-10) (Amerchol)

This composition was mixed with an aqueous, 1.5% strength hydrogen peroxide solution in the ratio 1:2 and applied to a dark blond normal hair tress. After a contact time of 30 min at 25° C., the tress was rinsed with water, subsequently shampooed and dried with a hairdryer.

The resulting tress had been colored light brown.

EXAMPLE 5

| | |
|---|---|
| Ammonium carbopol solution, 1% strength in water | 17.25 |
| Ammonium rohagit solution, 6% strength in water | 5.25 |
| Oleth-7 | 5.70 |
| Potassium olein soap, 12.5% strength in water | 12.75 |
| Potassium castor oil soap, 12.5% strength in water | 3.45 |
| Plantaren ® 2000 | 0.53 |
| Titanium dioxide anatase, type AS 05 | 0.48 |
| Cetiol ® V | 3.45 |
| Cetyl alcohol | 16.80 |
| Glycerol monostearate NSE | 2.85 |
| Phospholipid SV[11] | 0.85 |
| Tetrasodium EDTA | 0.46 |
| Silica, highly dispersed, pyrogenic | 0.11 |
| p-Tolylenediamine | 2.41 |
| Resorcinol | 0.86 |
| 3-Aminophenol | 0.26 |
| 1-Methoxy-2-amino-4-(2-hydroxyethylamino)benzene | 0.11 |
| 1,2-Propylene glycol USP | 1.05 |
| Methoxybutanol | 1.43 |
| Ammonia, 25% strength in water | ad pH 9.0 |
| Ascorbic acid | 0.06 |
| Gafquat ® 755N[12] | 0.50 |
| Perfume | 0.43 |
| Water | ad 100.00 |

[11]Compound of the formula (I) (about 41.5% active substance; INCI name: Stearamidopropyl PG-Dimonium Chloride Phosphate (and) Cetyl Alcohol) (Mona)
[12]Quaternized vinylpyrrolidone-dimethylaminoethyl methacrylate copolymer diethyl sulfate (about 19% active substance; INCI name: Polyquaternium-11) (ISP)

This composition was mixed with an aqueous, 6% strength hydrogen peroxide solution in the ratio 1:1 and applied to a light brown, 50% gray normal hair tress. After a contact time of 30 min at 25° C., the tress was rinsed with water, subsequently shampooed and dried with a hairdryer. The resulting tress had been colored dark brown and had very good gray coverage.

EXAMPLE 6

| | |
|---|---|
| Ammonium carbopol solution, 1% strength in water | 17.25 |
| Ammonium rohagit solution, 6% strength in water | 5.25 |
| Oleth-7 | 5.70 |
| Potassium olein soap, 12.5% strength in water | 12.75 |
| Potassium castor oil soap, 12.5% strength in water | 3.45 |
| Plantaren ® 2000 | 0.53 |
| Titanium dioxide anatase, type AS 05 | 0.48 |
| Cetiol ® V | 3.45 |
| Cetyl alcohol | 16.80 |
| Glycerol monostearate NSE | 2.85 |
| Phospholipid SV | 0.85 |
| Tetrasodium EDTA | 0.46 |
| Silica, highly dispersed, pyrogenic | 0.11 |
| p-Tolylenediamine | 2.12 |
| Resorcinol | 0.63 |
| 3-Aminophenol | 0.20 |
| 1-Methoxy-2-amino-4-(2-hydroxyethylamino)benzene | 0.05 |
| 1,2-Propylene glycol USP | 1.05 |
| Methoxybutanol | 1.43 |
| Ammonia, 25% strength in water | ad pH 8.9 |
| Ascorbic acid | 0.06 |
| Crotein ® C[13] | 0.30 |
| Perfume | 0.43 |
| Water | ad 100.00 |

[13]Gelatin hydrolyzate (about 93% active substance; INCI name: Hydrolyzed Collagen) (Croda)

This composition was mixed with an aqueous, 3% strength hydrogen peroxide solution in the ratio 1:1 and applied to a medium blond normal hair tress. After a contact time of 30 min at 25° C., the tress was rinsed with water, subsequently shampooed and dried with a hairdryer.

The resulting tress had been colored medium brown.

EXAMPLE 7

| | |
|---|---|
| Ammonium carbopol solution, 1% strength in water | 17.25 |
| Ammonium rohagit solution, 6% strength in water | 5.25 |
| Oleth-7 | 5.70 |
| Potassium olein soap, 12.5% strength in water | 12.75 |
| Potassium castor oil soap, 12.5% strength in water | 3.45 |
| Plantaren ® 2000 | 0.53 |
| Titanium dioxide anatase, type AS 05 | 0.48 |
| Cetiol ® V | 3.45 |
| Cetyl alcohol | 16.80 |
| Glycerol monostearate NSE | 2.85 |
| Phospholipid SV | 0.85 |
| Tetrasodium EDTA | 0.46 |
| Silica, highly dispersed, pyrogenic | 0.11 |
| p-Tolylenediamine | 0.84 |
| Resorcinol | 0.21 |
| 3-Aminophenol | 0.05 |
| 4-Chlororesorcinol | 0.16 |
| 1,2-Propylene glycol USP | 1.05 |
| Methoxybutanol | 1.43 |
| Ammonia, 25% strength in water | ad pH 9.0 |
| Ascorbic acid | 0.06 |
| Gluadin ® WK[14] | 0.70 |

| | |
|---|---|
| Perfume | 0.43 |
| Water | ad 100.00 |

[14]Wheat protein hydrolzate/fatty acid condensate (about 30% active substance; INCI name: Sodium Cocoyl Hydrolyzed Wheat Protein) (Henkel)

This composition was mixed with an aqueous, 3% strength hydrogen peroxide solution in the ratio 1:2 and applied to a medium blond normal hair tress. After a contact time of 30 min at 25° C., the tress was rinsed with water, subsequently shampooed and dried with a hairdryer.

The resulting tress had been colored dark blond.

EXAMPLE 8

| | |
|---|---|
| Ammonium carbopol solution, 1% strength in water | 17.25 |
| Ammonium rohagit solution, 6% strength in water | 5.25 |
| Oleth-7 | 5.70 |
| Potassium olein soap, 12.5% strength in water | 12.75 |
| Potassium castor oil soap, 12.5% strength in water | 3.45 |
| Plantaren ® 2000 | 0.53 |
| Titanium dioxide anatase, type AS 05 | 0.48 |
| Cetiol ® V | 3.45 |
| Cetyl alcohol | 16.80 |
| Glycerol monostearate NSE | 2.85 |
| Phospholipid PTC[15] | 0.85 |
| Tetrasodium EDTA | 0.46 |
| Silica, highly dispersed, pyrogenic | 0.11 |
| p-Tolylenediamine | 2.41 |
| Resorcinol | 0.86 |
| 3-Aminophenol | 0.26 |
| 1-Methoxy-2-amino-4-(2-hydroxyethylamino)benzene | 0.11 |
| 1,2-Propylene glycol USP | 1.05 |
| Methoxybutanol | 1.43 |
| Ammonia, 25% strength in water | ad pH 9.1 |
| Ascorbic acid | 0.06 |
| Merquat ® 280[16] | 0.20 |
| Perfume | 0.43 |
| Water | ad 100.00 |

[15]Compound of the formula (I) about 47% active substance; INCI name: Cocamidopropyl Pg-Dimonium Chloride Phosphat) (Mona)
[16]Dimethyldiallylammmonium chloride-acrylic acid copolymer (about 35% active substance; INCI name: polyquaternium-22) (Chemviron)

This composition was mixed with an aqueous 6% strength hydrogen peroxide solution in the ratio 1:1 and applied to a light brown, 50% gray normal hair tress. After a contact time of 30 min at 25° C., the tress was rinsed with water, subsequently shampooed and dried with a hairdryer.

The resulting tress had been colored dark brown and had very good gray coverage.

EXAMPLE 9

| | |
|---|---|
| Ammonium carbopol solution, 1% strength in water | 17.25 |
| Ammonium rohagit solution, 6% strength in water | 5.25 |
| Oleth-7 | 5.70 |
| Potassium olein soap, 12.5% strength in water | 12.75 |
| Potassium castor oil soap, 12.5% strength in water | 3.45 |
| Plantaren ® 2000 | 0.53 |
| Titanium dioxide anatase, type AS 05 | 0.48 |
| Cetiol ® V | 3.45 |
| Cetyl alcohol | 16.80 |
| Glycerol monostearate NSE | 2.85 |
| Phospholipid PTC | 0.85 |
| Tetrasodium EDTA | 0.46 |
| Silica, highly dispersed, pyrogenic | 0.11 |
| p-Tolylenediamine | 2.12 |
| Resorcinol | 0.63 |
| 3-Aminophenol | 0.20 |
| 1-Methoxy-2-amino-4-(2-hydroxyethylamino)benzene | 0.05 |
| 1,2-Propylene glycol USP | 1.05 |
| Methoxybutanol | 1.43 |
| Ammonia, 25% strength in water | ad pH 9.1 |
| Ascorbic acid | 0.06 |
| Jaguar ® C-17[17] | 0.30 |
| Perfume | 0.43 |
| Water | ad 100.00 |

Guar hydroxypropyltrimethylammonium chloride (INCI name: Hydroxypropyltrimonium Chloride) (Rhodia Inc.)

This composition was mixed with an aqueous, 3% strength hydrogen peroxide solution in the ratio 1:2 and applied to a light brown normal hair tress. After a contact time of 30 min at 25° C., the tress was rinsed with water, subsequently shampooed and dried with a hairdryer.

The resulting tress had been colored medium brown.

EXAMPLE 10

| | |
|---|---|
| Ammonium carbopol solution, 1% strength in water | 17.25 |
| Ammonium rohagit solution, 6% strength in water | 5.25 |
| Oleth-7 | 5.70 |
| Potassium olein soap, 12.5% strength in water | 12.75 |
| Potassium castor oil soap, 12.5% strength in water | 3.45 |
| Plantaren ® 2000 | 0.53 |
| Titanium dioxide anatase, type AS 05 | 0.48 |
| Cetiol ® V | 3.45 |
| Cetyl alcohol | 16.80 |
| Glycerol monostearate NSE | 2.85 |
| Phospholipid PTC | 0.85 |
| Tetrasodium EDTA | 0.46 |
| Silica, highly dispersed, pyrogenic | 0.22 |
| p-Tolylenediamine | 1.33 |
| Resorcinol | 0.48 |
| 3-Aminophenol | 0.10 |
| 1-Methoxy-2-amino-4-(2-hydroxyethylamino)benzene | 0.02 |
| 1,2-Propylene glycol USP | 1.05 |
| Methoxybutanol | 1.43 |
| Ammonia, 25% strength in water | ad pH 9.0 |
| Ascorbic acid | 0.06 |
| Mirapol ® A15 | 0.19 |
| Perfume | 0.43 |
| Water | ad 100.00 |

This composition was mixed with an aqueous 6% strength hydrogen peroxide solution in the ratio 1:2 and applied to a dark blond normal hair tress. After a contact time of 30 min at 25° C., the tress was rinsed with water, subsequently shampooed and dried with a hairdryer.

The resulting tress had been colored light brown.

What is claimed is:

1. A composition for coloring keratin fibers comprising
(a) at least one tenside of formula (I)

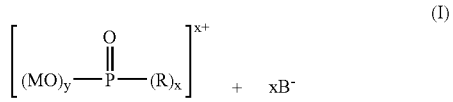

wherein y is an integer from 0 to 2, x is an integer from 1 to 3, and the sum of x and y is 3, wherein M is hydrogen, an alkali metal, alkaline earth metal, or an ammonium cation, or an alkyl radical having 1 to 4 carbon atoms that is optionally substituted by one or more hydroxyl groups, wherein B is a physiologically compatible anion, and wherein R is a radical of formula (II),

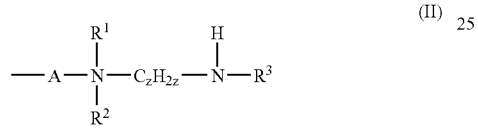

in which z is an integer from 1 to 4, $R^1$ and $R^2$, independently of one another, are a $C_1$ to $C_4$ alkyl radical, that is optionally substituted by one or more hydroxyl groups, or an acyl group, A is —O—$CH_2$—$CH_2$—$CH_2$—, —O—$CH_2$—$CH_2$— or —O—$CH_2$—CHOH—$CH_2$—, and $R^3$ is a branched or unbranched, saturated $C_8$ to $C_{18}$ acyl radical, or a branched or unbranched, monounsaturated or polyunsaturated $C_8$ to $C_{18}$ acyl radical;

(b) at least one conditioning component comprising a cationic polymer; and (c) at least one dye or dye precursor, or combinations thereof.

2. The composition of claim 1, wherein the composition further comprises an anionic tenside.

3. The composition of claim 1 wherein the conditioning component comprising a cationic polymer also contains a quaternary nitrogen compound in the form of an ammonium group.

4. The composition of claim 1 wherein the conditioning component comprises a quaternized cellulose derivative.

5. The composition of claim 1 wherein the cationic polymer comprises Polyquaternium-2.

6. The composition of claim 1 wherein the conditioning component is present in the composition in an amount of from 0.05 to 5% by weight.

7. The composition of claim 1 wherein the conditioning component is present in the composition in an amount of from 0.1 to 2% by weight.

8. The composition of claim 1 wherein the dye precursor comprises at least one oxidation dye precursor of the developer type.

9. The composition of claim 1 wherein the dye precursor is selected from the group consisting of 5,6-dihydroxyindole and 5,6-dihydroxyindoline.

10. The composition of claim 1 wherein the dye or dye precursor comprises at least one substantive dye, or natural dye, or combinations thereof.

11. The composition of claim 1 wherein the tenside of formula I comprises at least one compound selected from Linoleamidopropyl PG-Dimonium Chloride Phosphate, Cocamidopropyl PG-Dimonium Chloride Phosphate or Stearamidopropyl PG-Dimonium Chloride Phosphate, or combinations thereof.

12. The composition of claim 11 wherein the conditioning component comprises Polyquaternium 2.

13. A method for coloring keratin fibers comprising applying to keratin fibers a composition comprising
(a) at least one tenside of formula (I)
wherein y is an integer from 0 to 2, x is an integer from 1 to 3, and the sum of x and

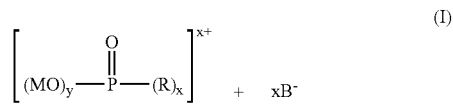

y is 3, wherein M is hydrogen, an alkali metal, alkaline earth metal, or an ammonium cation, or an alkyl radical having 1 to 4 carbon atoms that is optionally substituted by one or more hydroxyl groups, wherein B is a physiologically compatible anion, and wherein R is a radical of formula (II),

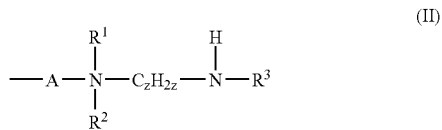

in which z is an integer from 1 to 4, $R^1$ and $R^2$, independently of one another, are a $C_1$ to $C_4$ alkyl radical, that is optionally substituted by one or more hydroxyl groups, or an acyl group, A is —O—$CH_2$—$CH_2$—$CH_2$—, —O—$CH_2$—$CH_2$— or —O—$CH_2$—CHOH—$CH_2$—, and $R^3$ is a branched or unbranched, saturated $C_8$ to $C_{18}$ acyl radical, or a branched or unbranched, monounsaturated or polyunsaturated $C_8$ to $C_{18}$ acyl radical;

(b) at least one conditioning component comprising a cationic polymer; and (c) at least one dye or dye precursor, or combinations thereof.

14. The method of claim 13 wherein the tenside of formula I comprises at least one compound selected from Linoleamidopropyl PG-Dimonium Chloride Phosphate, Cocamidopropyl PG-Dimonium Chloride Phosphate or Stearamidopropyl PG-Dimonium Chloride Phosphate, or combinations thereof.

15. The method of claim 13 wherein the composition further comprises an anionic tenside.

* * * * *